(12) United States Patent
Natsch et al.

(10) Patent No.: US 7,388,105 B2
(45) Date of Patent: Jun. 17, 2008

(54) COMPOUNDS AND USE TO REDUCE THE FORMATION OF MALODOUR

(75) Inventors: Andreas Natsch, Uetikon (CH); Felix Flachsmann, Duebendorf (CH)

(73) Assignee: Givaudan S.A., Vernier (CH)

( * ) Notice: Subject to any disclaimer, the term of this patent is extended or adjusted under 35 U.S.C. 154(b) by 61 days.

(21) Appl. No.: 11/584,686

(22) Filed: Oct. 20, 2006

(65) Prior Publication Data

US 2007/0092476 A1    Apr. 26, 2007

Related U.S. Application Data

(60) Provisional application No. 60/729,285, filed on Oct. 21, 2005.

(51) Int. Cl.
*C07C 228/04* (2006.01)
*A01N 47/12* (2006.01)

(52) U.S. Cl. .................. 562/443; 562/442; 514/478; 514/479; 514/489

(58) Field of Classification Search .............. None
See application file for complete search history.

(56) References Cited

U.S. PATENT DOCUMENTS 6,054,479 A * 4/2000 Yu et al. .................. 514/553

OTHER PUBLICATIONS

Andreas Natch, et al., Isolation of a Bacterial Enzyme Releasing Axillary Malodor and Its Use As a Screening Target For Novel Deodorant Formulations, International Journal of Cosmetic Science 27 (2), 115-122. doi: 10.111/j.1467-2494.2004.00255.x (and podium proceedings, pp. 318-322, 23rd Congress IFSCC, Orlando 2004, The Society of Cosmetic Chemists, New York NY, USA).

* cited by examiner

*Primary Examiner*—Yvonne Eyler
*Assistant Examiner*—Yevegeny Valenrod
(74) *Attorney, Agent, or Firm*—Curatolo Sidoti Co., LPA; Joseph G. Curatolo; Salvatore A. Sidoti

(57) ABSTRACT

Malodour formation reducing compounds alpha-N-(3-Methyl-5-phenylpentanoxycarbonyl)-L-glutamine, alpha-N-(2-Methyl-5-phenylpentanoxycarbonyl)-L-glutamine, and alpha-N-(2,4-Dimethyl-4-phenylbutanoxycarbonyl)-L-glutamine, and their salts, compositions comprising such compounds, including cosmetic products, personal care products, and deodorant products, and methods forming such products and their use. The compounds are useful to reduce the formation of human malodour resulting from bacterial degradation of compounds naturally present in sweat, in particular axilliary malodour.

11 Claims, No Drawings

COMPOUNDS AND USE TO REDUCE THE FORMATION OF MALODOUR

CROSS REFERENCE TO RELATED APPLICATIONS

This application claims the benefit of the filing date of U.S. Provisional Application for Patent Ser. No. 60/729,285 filed Oct. 21, 2005 which is hereby incorporated herein by reference in its entirety.

BACKGROUND

Disclosed are methods, compounds and compositions useful for the prevention or reduction of human malodour, in particular human axillary malodour.

It is known that fresh sweat is odourless and that odour is only formed upon contact of sweat with skin bacteria (for example bacteria of the genera of *Staphylococcus* and *Corynebacteria*), and it is believed that odourless molecules present in sweat are degraded by bacteria colonizing the axilla. It is generally accepted that highly unpleasant malodour is released from fresh sweat mainly by the *Corynebacteria* genus of bacteria.

It has been suggested to treat malodour by eliminating the bacteria that are causing it. Indeed, commercially-available deodorants often contain antibacterial compounds that inhibit the growth of skin microflora over a broad range of species. Antibacterial compounds currently used in deodorant products include, for example, the broad band antibacterial and antimicrobial Triclosan (2,4,4'-trichloro-2'hydroxy-diphenyl-ether). However, a draw-back to the use of antibacterials is the potential for disturbing the equilibrium of the skin's natural microflora.

Fatty acids are known to play a role in axillary malodour, and are characterised by a particularly unpleasant smell. Alpha-N-acyl-glutamine substrates have been shown to be the main precursors of axilla malodour and they are cleaved by the enzyme N-α-acyl-glutamine-aminoacylase to form unpleasantly smelling fatty acids (A. Natsch et al., Journal of Biological Chemistry 2003, 278(8), 5718-5727).

The applicants have identified specific inhibitors of the enzyme (WO 02/092024). Among many other compound groups, these include alpha-N-acyl-L-glutamines or carbamates of L-glutamine.

The malodour precursor compounds are substrates that may generally be described as derivatives of L-glutamine, in particular L-glutamine derivatives wherein the alpha-N atom of the L-glutamine residue is acylated with a residue of a malodorous compound, in particular a fatty acid residue, more particularly a short chain, branched fatty acid residue. One example of such a precursor compound that was isolated from human sweat has the structure:

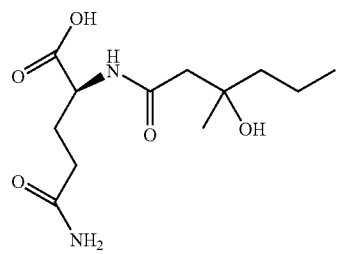

Cleavage of this substrate at the alpha-N position releases the 3-hydroxy-3-methyl-hexanoic acid, itself having a pungent odour, which dehydrates to give 3-methyl-3-hexenoic acid which is another key malodour volatile in human sweat.

The AMRE enzyme may cleave substrates for a wide variety of different smelling and non-smelling acids and other compounds. In addition to amide bonds, it may cleave carbamate bonds at the alpha-N position thereby mediating the release of an alcohol, $CO_2$ and L-glutamine.

The applicants now have found that malodour can be significantly reduced by certain alternative substrates that reduce the formation of unpleasantly-smelling cleavage products and instead produce cleavage products that are neutral or olfactorily pleasant.

DETAILED DESCRIPTION

Applicants found that certain identified alternative substrates work particularly well to reduce the formation of malodourous acid cleavage products from odourless fresh sweat and reduce axillary malodour in vivo. These alternative substrates have a particularly high activity in reducing the release of malodourous acids from N-acyl-glutamine substrates.

In one embodiment, a compound is provided, that may be at least one component selected from the group consisting of alpha-N-(3-Methyl-5-phenylpentanoxycarbonyl)-L-glutamine, alpha-N-(2-Methyl-5-phenylpentanoxycarbonyl)-L-glutamine, alpha-N-(2,4-Dimethyl-4-phenylbutanoxycarbonyl)-L-glutamine, salts thereof, and mixtures thereof.

A method for reducing malodour is provided, the method comprising utilizing a compound selected from the group consisting of alpha-N-(3-Methyl-5-phenylpentanoxycarbonyl)-L-glutamine, alpha-N-(2-Methyl-5-phenylpentanoxycarbonyl)-L-glutamine, alpha-N-(2,4-Dimethyl-4-phenylbutanoxycarbonyl)-L-glutamine, salts thereof, and mixtures thereof.

In another embodiment, a composition is provided comprising a malodour formation-reducing concentration of at least one compound, selected from the group consisting of alpha-N-(3-Methyl-5-phenylpentanoxycarbonyl)-L-glutamine, alpha-N-(2-Methyl-5-phenylpentanoxycarbonyl)-L-glutamine, alpha-N-(2,4-Dimethyl-4-phenylbutanoxycarbonyl)-L-glutamine, salts thereof, and mixtures thereof, in a dermatologically-acceptable formulation for a cosmetic product, personal care product or deodorant product. Suitable formulations are well known in the art.

Compounds hereinabove defined display a reduction of malodour formation at sufficient concentration in a dermatologically-acceptable formulation or cosmetic product, personal care product, or deodorant product. A sufficient concentration may be, for example, about 0.1 to about 3%, about 0.5 to about 1.5%, or about 0.5 to about 1% (all percentages weight/weight).

In one embodiment, a product is also provided, the product comprising a compound, as hereinabove defined, wherein the product is at least one selected from the group consisting of a cosmetic product, a personal care product and a deodorant product, in particular products directly applied to the skin, including sticks, roll-ons, pump-sprays, aerosols, soaps, powders, solutions, gels, creams, balms and lotions, to reduce the formation of malodour, in particular axilliary malodour.

In another embodiment, a method of forming a product, as hereinabove defined, is also provided, the method comprising providing a composition, said composition containing at least one compound selected from the group consisting of alpha-N-(3-Methyl-5-phenylpentanoxycarbonyl)-L-glutamine, alpha-N-(2-Methyl-5-phenylpentanoxycarbonyl)-L-glutamine, alpha-N-(2,4-Dimethyl-4-phenylbutanoxycarbonyl)-L-glutamine, salts thereof, and mixtures thereof, in a dermatologically acceptable formulation.

In one embodiment, the compound may be utilized in the product in a concentration sufficient to provide the desired malodour formation-reducing activity, for example, in a concentration of about 0.1 to about 3%, about 0.5 to about 1.5%, or about 0.5 to about 1% (all percentages weight/weight). Higher concentrations than 3% may also be employed (for example up to 5% or higher), though the effect will not necessarily increase and high concentrations will not usually be necessary. Similarly, when used in combination with other malodour reducing actives, the compound concentration may be lowered to a minimum of about 0.05%.

According to other embodiments, the method of reducing the formation of malodour comprises applying a product as hereinabove defined in a sufficient amount and at sufficient intervals, for example once or twice daily, to the skin.

The compounds defined above may also be used in their ionic form (salt), together with a counter-ion. Illustrative examples of useful cations to form a salt with the compounds hereinabove described include sodium, potassium, calcium, magnesium, and alkylammonium. Illustrative examples of useful alkylammonium ions are tetraaklyammonium ions, and alkylpyridinium ions. Illustrative examples of useful tetraalkylammonium ions are N,N-dimethyl-N-ethyl-dodecylammonium, and N,N-dimethyl-N-ethyl-hexadecylammonium. Illustrative examples of alkylpyridinium ions are N-dodecylpyridinium, and N-octadecylpyridinium. The illustrative examples should not be construed as limiting in any manner.

Further illustrative examples of useful ions to form a salt with compounds as hereinabove described are ions of the following compounds: amino compounds, for example diisopropyl-amine, ethanolamine, diethanolamine and aminomethylpropanol; and amino acids (for example lysine), or derivatives of aminoacids, for example alkylaminoalkylglycines (for example N-laurylaminopropyl glycine). The illustrative examples should not be construed as limiting in any manner.

The compounds as hereinabove described in their ionic form, in particular with alkylammonium ions or ions of amino compounds, may be rendered sufficiently soluble to be included in formulations containing water, organic solvents (for example ethanol), or other solvents used in cosmetic products, consumer products, or deodorant products.

The compounds defined above may be combined with other active ingredients used in deodorants. Illustrative examples include Triclosan™; chelating agents such as EDDS (ethylenediamine-disuccinate), DTPA (diethylendiaminepentaacetate), EDTA (ethylenediamine-tetraacetate); biocidal compounds such as Cosmocil® CQ (Polyhexanide), Sensiva® SC 50 (3((2-ethylhexyl)oxy)1,2-propanediol, Schülke and Mayr). The illustrative examples should not be construed as limiting in any manner.

Inventors' publication in *International Journal of Cosmetic Science* 27 (2), 115-122, "Isolation of a Bacterial Enzyme Releasing Axillary Malodor And Its Use As A Screening Target For Novel Deodorant Formulations" by Andreas Natsch et al. (and podium proceedings, pages 318-322, 23$^{rd}$ Congress IFSCC, Orlando 2004, The Society of Cosmetic Chemists, New York N.Y., USA) is explicitly incorporated herein by reference in its entirety, as if written out fully below.

The following examples are set forth merely to illustrate the effect of the treatment of the samples with certain substrates. The illustrative examples should not be construed as limiting the compounds, compositions, products or methods of reducing the formation of malodour in any manner.

EXAMPLE 1

Alternative Substrates of N-α-acyl-glutamine-aminoacylase

In a sample, the enzyme alpha-N-acyl-glutamine-aminoacylase was used at a concentration of 36 ng/ml in Buffer A (50 mM NaCl; 50 mM NaH$_2$PO$_4$/K$_2$HPO$_4$; pH 7). To each sample, alpha-N-decanoyl-glutamine or alpha-N-(E)-3-methyl-2-hexenoyl-glutamine was added at a final concentration of 0.2 mM as a substrate.

Further, to each sample various competitive substrates are added as shown in Table 1 below at different concentrations as indicated.

The resulting samples with enzyme, substrate and competitive substrate were incubated for 15 minutes, acidified to pH 2 with HCl and extracted with methyl tert butyl ether (MTBE). The release of decanoic acid ("DA") or (E)-3-methyl-2-hexenoic acid ("MH") was assayed and compared to a positive control that did not contain a competitive substrate (enzyme and substrate only). The percentage of the reduction of the release when compared to the positive control is given in Table 1 (equals inhibition of the enzmye).

The following compounds were tested:

1. alpha-N-(3-Methyl-5-phenylpentanyloxycarbonyl)-L-glutamine

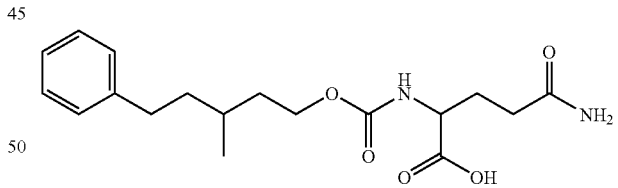

2. alpha-N-(10-undecenoyl)-L-glutamine

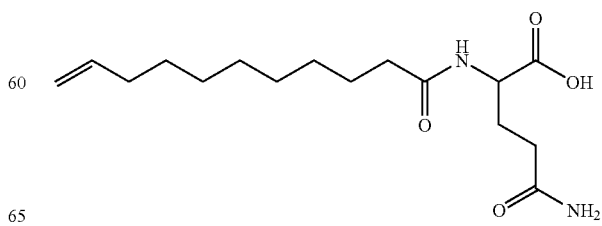

3. alpha-N-(2-isopropyl-5-methylcyclohexanyloxycarbonyl)-L-glutamine

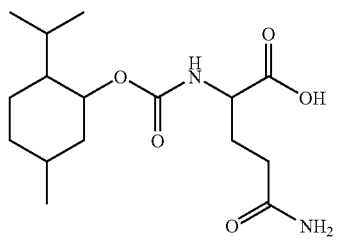

4. alpha-N-(3,7-dimethyl-oct-6-enyloxycarbonyl)-L-glutamine

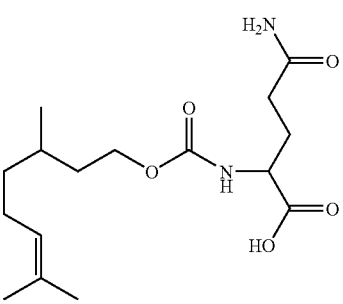

5. alpha-N-Butyloxycarbonyl-L-glutamine

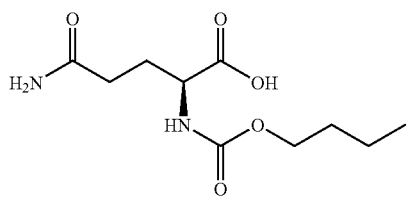

6. alpha-N-(4-tert-Butylcyclohexyloxycarbonyl)-L-glutamine

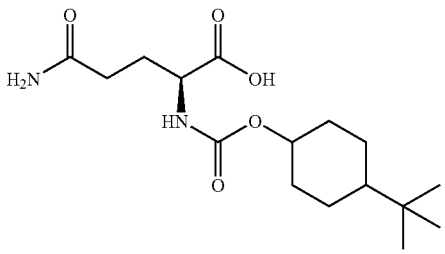

Table 1 below lists the the results for the relative reduction/inhibition of acid release for the compounds tested.

| Compound No. | Concentration Tested compound [mM] | % Inhibition (DA) | % Inhibition (MH) |
|---|---|---|---|
| 1 | 0.4 | n.d. | 78.3 |
| 2 | 0.4 | n.d. | 24.2 |
| 3 | 0.4 |  | 33.9 |
| 4 | 0.4 | n.d. | 16.1 |
| 5 | 0.4 | n.d. | 0 |
| 6 | 0.4 | n.d. | 28.5 |
| 1 | 0.2 | 64.4 | 58.1 |
| 2 | 0.2 | 15.6 | 2.1 |
| 3 | 0.2 | 27.2 | 16.5 |
| 4 | 0.2 | 34.6 | 17.1 |
| 5 | 0.2 | 10.4 | 0 |
| 6 | 0.2 | 21.2 | 14.8 |
| 1 | 0.1 | 57.0 | 35.5 |
| 2 | 0.1 | 2.2 | 0 |
| 3 | 0.1 | 19.3 | 7.4 |
| 4 | 0.1 | 13.8 | −0.3 |
| 5 | 0.1 | 6.8 | 1.1 |
| 6 | 0.1 | 14.3 | 4.9 |
| 1 | 0.05 | 38.3 | n.d. |
| 2 | 0.05 | 0.9 | n.d. |
| 4 | 0.05 | 15.9 | n.d. |
| 5 | 0.05 | 6.7 | n.d. |
| 6 | 0.05 | 11.3 | n.d. | n.d. = not determined

These results show that alpha-N-(3-Methyl-5-phenylpentanoxycarbonyl)-L-glutamine is a particularly good inhibitor of $N_\alpha$-acyl-glutamine-aminoacylase.

EXAMPLE 2

Reduction of Axilla Malodour In Vivo by Deodorant Products Containing Alpha-N-(3-Methyl-5-phenylpentanoxycarbonyl)-L-glutamine Alpha-N-(3-Methyl-5-phenylpentanoxycarbonyl)-L-glutamine is added to various deodorant formulations. Four roll-on deodorant formulations are prepared by mixing the ingredients in the amounts in % as indicated in Table 2 below:

TABLE 2

|  | Formula | | | |
|---|---|---|---|---|
|  | Standard formula | Formula A | Formula B | Placebo |
| Dipropylene Glycol (DPG) | 15.0 | 15.0 | 15.0 | 15.0 |
| Propylenglycol (PG) | 5.0 | 5.0 | 5.0 | 5.0 |
| Triclosan (antibacterial) | 0.3 | # | # | # |
| Alpha-N-(3-Methyl-5-phenylpentanoxycarbonyl)-L-glutamine | # | 2.5 | 1.00 | # |
| Thickener (hydroxyethylcellulose, Natrosol ® 250 HHR, from Hercules-Aqualon) | 0.35 | 0.35 | 0.35 | 0.35 |
| PEG-40 hydrogenated castor oil (Cremophor ® CO 40, from BASF) | 5.0 | 5.0 | 5.0 | 5.0 |
| Water | Add to 100% | Add to 100% | Add to 100% | Add to 100% |

The deodorants are applied to the axilla of 14 panelists (7 male and 7 female). The test is repeated three times on three consecutive days. For comparison, the placebo without malodour counteracting substances is applied to one axilla as a control, and on the contralateral side one of the malodour counteracting samples (standard formulation with antibacterial, formula A, formula B) is applied.

During a period of three weeks, one product is tested each week. 8 hours after each application, 3 trained malodour judges rate the malodour intensity in the axilla of each subject. The rating of malodour is done according to common practice in the industry using the standard 1-10 scale (1=little noticed MO, 2=slightly noticed MO, 3=slight MO, 4=slight to moderate, 5=moderate, 6=slightly strong, scores 7-10 are usually not detected).

A score equaling that of the placebo means that no effect of the tested active ingredient is observed and the formulation does not reduce malodour. A score lower than that of the placebo means that a reduction in malodour is achieved by the added active ingredient in the tested formulation.

Table 3 below lists the results.

TABLE 3

|  | Malodour score Axilla 1 | Malodour score Placebo Axilla 2 | Difference | Test |
|---|---|---|---|---|
| Standard formula (with Triclosan) | 4.22 | 4.33 | −0.11 | 0.2610 |
| Formula A | 3.97 | 4.47 | −0.50 | 0.0001 |
| Formula B | 3.99 | 4.42 | −0.43 | 0.0003 |

A standard formulation with the known deodorant active antibacterial Triclosan a has a malodour score only slightly lower/better (less malodour detected) than the placebo. Formulas A and B score significantly lower/better (compare statistical T test numbers) than the placebo (control without active substances) in the malodour score, and therefore significantly reduce malodour.

EXAMPLE 3

Reduction of Axilla Malodour In Vivo by Formula B Deodorant Containing Alpha-N-(3-Methyl-5-phenylpentanoxycarbonyl)-L-glutamine Formula B and the placebo (see example 2) are applied by 25 test consumers. Consumers use the product in the morning and self-evaluate of axilla malodour in the evening. 26-29% of consumers do not note any malodor during the evaluation in the evening, both for placebo and formula B. Among the remaining 70% of tested consumers, the proportion of responses noting moderate to strong malodor is reduced from 44% to 20% with the formula B when compared to the placebo. Table 4 below lists the results.

TABLE 4

|  | 0-none | 1-Slight | 2-Moderate | 3-Strong | None and Slight | Moderate and strong |
|---|---|---|---|---|---|---|
| Formula B | 29 | 51 | 14 | 6 | 80 | 20 |
| Placebo | 26 | 30 | 34 | 10 | 56 | 44 |

In formula B-2, the malodour reducing active Alpha-N-(3-Methyl-5-phenylpentanoxycarbonyl)-L-glutamine of formula B is replaced with the similar alpha-N-cis-3-hexenyloxycarbonylglutamine carbamate). For formula B-2, almost no malodour reduction effect is observed. Table 5 below lists the results.

TABLE 5

|  | 0-none | 1-Slight | 2-Moderate | 3-Strong | None and Slight | Moderate and strong |
|---|---|---|---|---|---|---|
| Formula B-2 | 39 | 41 | 15 | 5 | 80 | 20 |
| Placebo | 40 | 35 | 20 | 4 | 75 | 24 |

EXAMPLE 4

Alternative to Compound 1: alpha-N-(2-Methyl-5-phenylpentanoxycarbonyl)-L-glutamine As an alternative to compound 1 of examples 1-3, the following compound was used to produce similar results as an alternative enzyme substrate in malodour formation reducing effect:

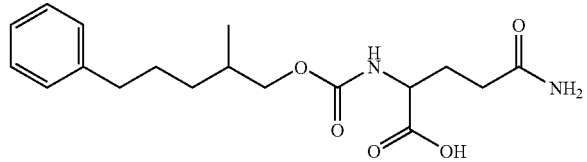

EXAMPLE 5

Alternative to Compound 1: alpha-N-(2,4-Dimethyl-4-phenylbutanoxycarbonyl)-L-glutamine As an alternative to compound 1 of example 1-3, the following compound was used.

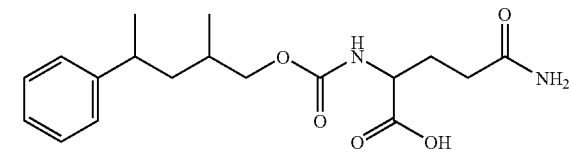

Similar results with regard to the malodour formation reducing effect as described in examples 1-3 were observed.

It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

We claim:
1. A compound selected from the group consisting of alpha-N-(3-Methyl-5-phenylpentanoxycarbonyl)-L-glutamine, alpha-N-(2-Methyl-5-phenylpentanoxycarbonyl)-L-glutamine, alpha-N-(2,4-Dimethyl-4-phenylbutanoxycarbonyl)-L-glutamine and salts thereof.
2. A method of reducing axilliary malodour comprising administering a compound selected from the group consisting of alpha-N-(3-Methyl-5-phenylpentanoxycarbonyl)-L-glutamine, alpha-N-(2-Methyl-5-phenylpentanoxycarbo- nyl)-L-glutamine, alpha-N-(2,4-Dimethyl-4-phenylbutanoxycarbonyl)-L-glutamine, salts thereof, and mixtures thereof.

3. A composition comprising a malodour formation reducing concentration of a compound selected from the group consisting of alpha-N-(3-Methyl-5-phenylpentanoxycarbonyl)-L-glutamine, alpha-N-(2-Methyl-5-phenylpentanoxycarbonyl)-L-glutamine, alpha-N-(2,4-Dimethyl-4-phenylbutanoxycarbonyl)-L-glutamine, salts thereof, and mixtures thereof, in a dermatologically-acceptable formulation for a cosmetic product, personal care product or deodorant product.

4. The composition according to claim 3, wherein the compound is present in a concentration of about 0.1% to about 3% (w/w).

5. A product comprising a compound selected from the group consisting of alpha-N-(3-Methyl-5-phenylpentanoxycarbonyl)-L-glutamine, alpha-N-(2-Methyl-5-phenylpentanoxycarbonyl)-L-glutamine, alpha-N-(2,4-Dimethyl-4-phenylbutanoxycarbonyl)-L-glutamine and salts thereof, or mixtures thereof, wherein the product is selected from the group consisting of cosmetic products, personal care products, and deodorant products.

6. The product according to claim 5, wherein the product is adapted to be applied to the skin, wherein the product is selected from the group consisting of sticks, roll-ons, pump-sprays, aerosols, soaps, powders, solutions, gels, creams, balms and lotions.

7. The product according to claim 5 wherein the compound is present in combination with another active deodorant ingredient.

8. A method of forming the product as defined in claim 5, comprising providing a composition, said composition containing the compound in a dermatologically acceptable formulation.

9. The method of claim 8, wherein the product is selected from the group consisting of sticks, roll-ons, pump-sprays, aerosols, soaps, powders, solutions, gels, creams, balms and lotions.

10. A method of reducing the formation of malodour by applying the product as defined in claim 5, in a sufficient amount and sufficient intervals to the skin.

11. The method of claim 10, wherein the product is selected from the group consisting of sticks, roll-ons, pump-sprays, aerosols, soaps, powders, solutions, gels, creams, balms and lotions.

* * * * *